United States Patent [19]

Eibl et al.

[11] Patent Number: 4,904,641

[45] Date of Patent: Feb. 27, 1990

[54] METHOD OF INACTIVATING REPRODUCIBLE FILTERABLE PATHOGENS IN BLOOD PLASMA PRODUCTS

[75] Inventors: Johann Eibl; Otto Schwarz; Fritz Elsinger, all of Vienna; Günter Wöber, Oberwaltersdorf; Anton Philapitsch, Ebenfurth; Yendra Linnau, Vienna; Friedrich Dorner, Vienna; Karl Trambauer, Vienna; Wolfgang Frechinger, Vienna, all of Austria

[73] Assignee: Immuno Aktiengesellschaft für chemisch-medizinische Produkte, Vienna, Austria

[21] Appl. No.: 293,085

[22] Filed: Jan. 3, 1989

[30] Foreign Application Priority Data

Jan. 12, 1988 [AT] Austria .................................. 50/88

[51] Int. Cl.⁴ ..................... A61K 37/02; A61K 35/16
[52] U.S. Cl. ......................................... 514/2; 424/101; 514/7; 514/8
[58] Field of Search ................... 424/101; 514/2, 7, 8

[56] References Cited

U.S. PATENT DOCUMENTS

| | | |
|---|---|---|
| 3,041,242 | 6/1962 | Barr . |
| 4,379,085 | 4/1983 | Williams et al. . |
| 4,490,361 | 12/1984 | Heldebrant . |
| 4,522,751 | 6/1985 | Linnau et al. . |
| 4,640,834 | 2/1987 | Eibl et al. ........................... 424/101 |

Primary Examiner—Sam Rosen
Attorney, Agent, or Firm—Burns, Doane, Swecker & Mathis

[57] ABSTRACT

There is disclosed a method of inactivating reproducible filterable pathogens in blood plasma products by applying elevated temperatures. The blood plasma products are heat treated in a solid state in a closed inactivation container in the presence of specific amounts of water and organic compounds, provided that the water substantially remains physically bound to the blood plasma products, while the organic compound is present in a gaseous form in the atmosphere. The water content of the blood plasma products is 0.08 to 0.40. The concentration of the organic compounds in the gaseous phase is 0.01 to 10 g per liter of container volume.

5 Claims, No Drawings

METHOD OF INACTIVATING REPRODUCIBLE FILTERABLE PATHOGENS IN BLOOD PLASMA PRODUCTS

The invention relates to a method of inactivating reproducible filterable pathogens in blood plasma products by applying elevated temperatures.

Inactivation methods of this type have been dealt with comprehensively in the literature. The various methods include, i.a., heating of the blood products in an aqueous solution, optionally upon the addition of virucidal substances, in the presence of stabilizing agents, heating of the blood products in the dry state.

Thus, for instance, German Pat. No. 29 16 711 describes a method of treating coagulation factor-containing preparations in aqueous solutions by applying a temperature of from 30° C. to 100° C., wherein an amino acid and a monosaccharide, an oligosaccharide or a sugar alcohol are added to the solution of the coagulation factors.

In EP-A2 0 035 204 a method of inactivating aqueous protein solutions which may contain Factor VIII, fibronectin, globulin, fibrinogen and other proteins is disclosed, wherein the composition is mixed with a polyol and the mixture is heated to a temperature of from 60° C. to 75° C.

In U.S. Pat. No. 4,379,085 a method of thermally inactivating a plasma protein, such as $C_1$ inhibitor or Factor IX, in an aqueous solution in the presence of potassium or ammonium citrate is described.

In EP-A2 0 077 870 a virus-inactivation method is described, in which an aqueous solution containing Factor VIII is heated to a temperature of from 50° C. to 80° C. together with amino acids, monosaccharides, oligosaccharides, sugar alcohols and hydrocarbon-carboxylic acids or hydroxyhydrocarbon-carboxylic acids having 3 to 10 carbon atoms.

U.S. Pat. No. 3,041,242 describes heating dry human plasma followed by applying a lethal gas under high vacuum conditions for the purpose of killing the virus.

German Pat. No. 34 34 472 and EP-A2 0 240 750 describe the pasteurization of pulverous lyophilized plasma proteins suspended in a liquid thermal carrier, i.a., alcohol and fatty acid esters. Yet, the water content of the system is to be smaller than 0.01 and a possible effect of this measure on human pathogenic viruses in not reported.

Also does U.S. Pat. No. 4,490,361 describe heating of the suspension of a dry protein powder in an organic liquid.

In published PCT application WO No. 85/05273, Purcell describes the inactivation of lipid-containing viruses in the dry state with water-containing halohydrocarbons. Due to the low solubility of water in chloroform, which is the preferred halohydrocarbon, the water content of the system is less than 0.05 also there.

EP-A2 0 094 611 discloses a method of treating a Factor VIII-containing composition in the dry state with less than 0.05 (5% by weight) water by applying a temperature of at least 60° C. for the purpose of inactivating hepatitis viruses present.

Published PCT-application WO No. 82/03871 discloses a method of treating preparations containing blood coagulation enzymes by heating the same in the dry state to inactivate infectious viruses present; as the dry state, a state with less than 0.05 (5% by weight) water is defined.

Moreover, in U.S. Pat. No. 4,640,834 of Applicants, an inactivation method is described in which the blood products in solid state are adjusted to a content of water, methanol or ethanol of more than 0.05 (5% by weight) and less than 0.70 (70% by weight), preferably less than 0.40 (40% by weight), and are treated in a closed container at a temperature ranging between 50° and 121° C. by raising the partial vapor pressure of the water, methanol or ethanol.

According to further prior art, the heat treatment of an aqueous solution of the blood coagulation factors IX and X in the presence of sucrose and glycine is known from EP-B1 0 053 338, wherein the biologic activity of these coagulation factors is to be stabilized by the addition of 0.05 to 2M calcium ions.

Also European Pat. No. 0 137 428 is related to a method of producing a preparation of blood coagulation factors II, VII, IX and X by heating in an aqueous solution upon the addition of sucrose, glycine, calcium ions (1 to 50 mM) and a chelating agent.

All these methods, in common, endeavor to eliminate the potential infectivity of blood plasma products, yet by conserving their biologic activities to the major extent. In the case of the inactivation of heat stable viruses, e.g., hepatitis viruses, this goal has not been reached in a satisfactory manner so far.

The present invention aims at eliminating the difficulties faced so far and at providing an inactivation method by which a higher effectiveness of virus inactivation and, thus, a greater safety with regard to the transmission of pathogenic viruses are attained under comparable inactivation times and inactivation temperatures; at the same time, conservation of the biologic activity of the respective blood plasma product is to be largely ensured.

Departing from U.S. Pat. No. 4,640,834, this invention constitutes an improvement to, and further development of, the same by having found that a specific combination of an aqueous and an organic treating medium yields the best results.

Accordingly, with a method of inactivating reproducible filterable pathogens in blood plasma products by applying elevated temperatures, with the blood plasma products being heat treated in a solid state in a closed inactivation container in the presence of hydroxyl group-containing compounds whose concentration is more than 0.05 (5% by weight), relative to the blood plasma products, the invention consists in the combination of the following measures:

that the blood plasma products are adjusted to a water content of from 0.08 to 0.40 (8 to 40% by weight) before the heat treatment—whereby the water contained in the system substantially remains physically bound to the blood plasma products during the heat treatment—, and that, during the heat treatment of the blood plasma products, an organic compound from the group consisting of ethanol, acetic acid ethyl ester, diethyl ether, dimethylformamide, toluene, chloroform, n-heptane, 1,2-diacetoxy ethane and acetone, is provided in the gaseous phase of the container at a concentration of from 0.01 to 10 g of the organic compound per liter of container volume.

Advantageously, the heat treatment is carried out in the presence of calcium ions, the calcium ions either being admixed at any stage of the fractionation process of the blood plasma products prior to lyophilization, or the lyophilized product is moistened with water containing calcium ions. The addition of calcium ions induces an improved stabilization of the activities of the blood plasma products.

A preferred embodiment of the method according to the invention consists in that the blood plasma products are moistened with steam until the desired moisture content has been attained, the blood plasma products are placed into the inactivation container, and subsequently the organic compound is introduced into the container in gaseous form in order to adjust the desired concentration, whereupon the closed container containing the blood plasma products is brought to the inactivation temperature and is heated for the period of time required for virus inactivation.

Advantageously, moistening of the blood plasma products with steam is carried out under vacuum.

Preferably, the heat treatment is carried out at a temperature of from 50° to 80° C.

According to a preferred embodiment, the container atmosphere—before introducing the organic compound—is rendered free of oxygen by displacement with an inert gas, in particular, dry nitrogen.

The method according to the invention will be explained in more detail by way of the following examples:

EXAMPLE 1

A Factor VIII preparation was produced according to the method described in U.S. Pat. No. 4,522,751 and was freeze-dried. 350 g of the lyophilized bulk powder, which had a moisture content of 0.019, were introduced into an evacuatable container equipped with a steam supply, and the container was evacuated, with a pressure of 4 mbar adjusting. 90 ml of distilled water—which corresponds to a set moisture value of 0.2 (20% by weight)—were introduced into the container in steam form to moisten the powder, the pressure rising to 33 mbar. After a short time of action of the steam on the lyophilized material, an equilibrium pressure of 23 mbar resulted.

The moistening container was then swept with dry nitrogen and was brought to atmospheric pressure. The increase in weight of the powder was 85.5 g. The moistened powder was equilibrated for 24 hours and the water content was determined according to Karl Fischer (Scholz E., Z. analyt. Chem. 314, 567–571 (1983)).

In three aliquot samples water contents of 0.203/0.200/0.202 were found.

A partial amount of 162 g of the thus prepared moistened bulk powder was placed into a closeable evacuatable inactivation container equipped with gas feeds (volume 15.4 l) and evacuated two consecutive times to a pressure of 100 mbar; then, a pressure adjustment to ambient pressure was effected with dry nitrogen. Subsequently, the pressure within the inactivation apparatus was again lowered to 100 mbar and 3.85 g of ethanol in gaseous form were introduced through a gas feed; this corresponds to an amount of 0.25 g of ethanol/1 of the total volume of the inactivation container.

Subsequently, the pressure in the inactivation container was increased to ambient pressure with dry nitrogen, the container was closed and heated at 60° C. for 10 hours. During the heat treatment, a total pressure of 1,222 mbar and a dew point of 49.8° C. were measured within the container.

From the determination of the dew point, one may conclude how the water is distributed between the solid phase (lyophilisate) and the gaseous phase in the inactivation container during heating of the moist powder at 60° C. Direct measurement of the water content of the powder at 60° C. is not possible without disturbing the equilibrium in the closed system. However, the water content of the atmosphere and hence that of the lyophilisate may be calculated from the dew point measured in the gaseous phase of the closed inactivation container at 60° C. In doing so, the Factor VIII-containing material has shown to contain about 96% of its water content in the form of physically bound water even when heated to 60° C.

In detail, the calculation can be carried out with the help of the data indicated in Table I:

TABLE I

| Water content of moist Factor VIII-containing lyophilisate during heating at 60° C. | | | | | | | |
|---|---|---|---|---|---|---|---|
| 1 | 2 | 3 | 4 | 5 | 6 | 7 | 8 |
| Factor VIII-lyophilisate | Mass of moist product g | g Water per g moist product | Total amount of water in the system g | Volume of inactivation vessel l | Temperature °C./K. | Total pressure $p_{tot}$ mbar | Dew point (DP) °C. |
| | 162 | 0.20 | 32.4 | 15.4 | 60/333 | 1222 | 49.8 |
| 9 | 10 | 11 | 12 | 13 | 14 | 15 | |
| | | | | | H$_2$O in gaseous phase | | |
| $p_{H_2O}$/DP saturation steam pressure at dew point mbar | $p_{N_2}$/60 (cols. 7–9) mbar | $\dfrac{g_{H_2O} \text{ (gas)}}{g_{N_2}}$ (Equation 1) $0.643 \cdot \dfrac{\text{col. 9}}{\text{col. 10}}$ | $v_{1gN_2}$/60 (Equation 3) $2.97 \cdot \dfrac{\text{col. 6 K}}{\text{col. 10}}$ | $\dfrac{g_{H_2O} \text{ (gas)}}{l_{N_2}/60}$ $\dfrac{\text{col. 11}}{\text{col. 12}}$ | inactivation container col. 13 · col. 5 g | % of total water $\dfrac{\text{col. 14}}{\text{col. 4}} \cdot 100$ | |
| 122 | 1100 | 0.0713 | 0.8991 | 0.0793 | 1.22 | 3.8 | |

In this example, the water content of the moistened powder was 0.20 as determined according to Karl Fischer (col. 3 of Table I).

During the subsequent treatment of the moistened powder under nitrogen atmosphere at 60° in the closed inactivation container, a total pressure of 1,222 mbar (col. 7) and a dew point of 49.8° C. (col. 8) were measured. The measuring device was a Dew Point Hygrometer, Type 660 of EG & G Environmental Equipment. From the hygrometric and psychrometic tables of the Smithsonian Institution, the saturation vapor pressure pH$_2$O/DP of water may be read at the measured dew point (col. 9). By substracting this saturation pressure pH$_2$O/DP from the total pressure $p_{tot}$, the partial pressure of nitrogen at 60° C. pN₂/60 (col. 10=col. 7-col. 9) is obtained. With the help of these values, the expression gH₂O per gN₂(col. 11) in the gaseous phase may be calculated according to the following formula:

$$\frac{g_{H_2O}\ (gas)}{g_{N_2}} = \frac{MW\ H_2O}{MW\ N_2} \cdot \frac{p_{H_2O}/DP}{p_{N_2}} = 0.643 \cdot \frac{p_{H_2O}/DP}{p_{N_2}} \quad \text{Equation 1}$$

To transform the expression of column 11 into the illustrative expression gH₂O (gas) per liter N₂, the value in column 11 is divided by the volume of 1 g N₂ under the conditions of the inactivation container.

The mass of 1 l N₂ at 0° C. (=273K) and 760 mm Hg (=1 atm=1013 mbar) is 1.2505 g, and 1 g N₂ under these normal conditions has a volume of 0.800 l. According to the laws of Gay-Lussac and Boyle-Mariotte, the following equation is valid:

$$\frac{p_1 \cdot v_1}{T_1} = \frac{p_2 \cdot v_2}{T_2} \quad \text{Equation 2}$$

With the respective values of p₁, v₁, T₁ and p₂, v₂, T₂ at normal conditions and 60° C., there results $$\frac{1013 \cdot 0.800}{273} = \frac{p_N/60 \cdot v_{1gN}/60^*}{333} \quad \text{Equation 3}$$

*volume of 1 g N₂ at 60° C.

The sought value $v_{1gN/60}$ in liters (col. 12) is obtained by transformation of the Equation 3 and insertion of the value of col. 10.

$$v_{1gN}/60 = 2.97 \cdot \frac{333}{1100} = 0.8991\ (\text{col. 12})$$

By dividing the values of columns 11 and 12, the sought expression $g_{H_2O}$ per 1 N₂ at 60° C. in the gaseous phase is obtained (col. 13). Multiplication by the volume of the inactivation container (col. 5) yields the desired result: g water in the form of vapor in the inactivation vessel at 60° C. At this calculation, the error due to the volume of the lyophilisate was neglected.

Hence results that, at 60° C. in the inactivation container, only about 4% of the total amount of water is present in the gaseous phase, i.e., that even with an elevated temperature the major portion of the water remains physically bound to the lyophilisate.

The content of ethanol in the atmosphere can be determined by taking several gas samples of 20 ml each by means of an injection syringe and gas-chromatographically analyzing the same after having reached a temperature of 60° C. and adjustment of an equilibrium between the solid substances and the atmosphere within the container.

It was found that the ethanol content of the atmosphere amounted to 93.2 mg per liter of the container volume, from which it is apparent that nearly 40% of the available amount of ethanol is not associated with proteins but is present in the gaseous phase.

After the above-described heating at 60° C. for 10 hours, the inactivated bulk powder was removed and stored at a temperature of +2° to +8° C. The determination of the Factor VIII activity before and after the heat treatment showed a residual activity of 0.71 (71% yield of Factor VIII).

To assess the virus inactivation effect, the kinetics of the inactivation according to the invention of various model viruses was investigated in a parallel assay. In doing so, also the residual Factor VIII activity after inactivation was determined in virus-free samples after comparable heat treatments.

To follow the inactivation kinetics, aliquots of the above-described Factor VIII material in the form of an aqueous solution were mixed with a Vaccinia virus suspension in cell culture medium TCM 199 as well as with virus-free TCM 199, filled in several vials and freeze-dried. The freeze-dried Factor VIII concentrate was adjusted to a water content of 0.20 (20% by weight), was "gassed" with dry nitrogen as previously described and was heated to 60° C. for 10 hours in the closed vials. After 1, 3 and 10 hours, the virus titer was determined, the heat treated preparations each being dissolved in water and serially diluted with isotonic saline at a ratio of 1:10. The titer of the virus was determined by evaluating the cytopathic effect on sensitive Vero cells in a microtiter plate. The results were statistically evaluated and expressed as TCID₅₀ according to the formula by Reed and Muench (Reed J. L. and H. Muench; Amer. J. Hyg. 27, 493 (1938)).

In the same manner, the kinetics of the inactivation of the same Vaccinia virus was investigated when applying the method according to the invention, wherein an ethanol atmosphere of 0.25 g/l of container volume was maintained in the vial after adjustment of the water content to 0.20 (20% by weight) and "nitrogen gassing".

Table II indicates the remarkable progress achieved by the mode of operation according to the invention by using an alcoholic atmosphere under otherwise equal conditions, over the mode of operation known from U.S. Pat. No. 4,640,834 (prior art).

As a further model virus for the assessment of the inactivation kinetics according to the invention, bacteriophage X 174 was used and compared to the prior art. It is to be pointed out that both Vaccinia virus and bacteriophage X 174 are extremely heat stable viruses. The results obtained with these model viruses are suited to draw conclusions as to the effectiveness of the method according to the invention with regard to viruses that may occur in blood plasma products and whose inactivation is important to the safety of the products when applied in man, such as, e.g., HIV (transmitting AIDS), hepatitis B viruses, hepatitis NANB viruses, CMV, EBV.

TABLE II

Kinetics of virus inactivation and Factor VIII activity during heating at 60° C. of a freeze-dried Factor VIII preparation

| | Water content | Ethanol (g/l) | Vaccinia virus titer (TCID₅₀) after heating for | | | | residual Factor VIII activity after heating for | | | | |
|---|---|---|---|---|---|---|---|---|---|---|---|
| | | | 0 | 1 | 3 | 10 | 0 | 1 | 3 | 10 | hours |
| Combination acc. to inven- | 0.20 | 0.25 | $10^{4.4}$ | $10^{3.5}$ | $10^{1.2}$ | $<10^1$ | 0.92 | 0.82 | 0.80 | 0.65 | |

TABLE II-continued

Kinetics of virus inactivation and Factor VIII activity during heating at 60° C. of a freeze-dried Factor VIII preparation

| | | | | | | | | | | |
|---|---|---|---|---|---|---|---|---|---|---|
| tion of org. compound + water | | | | | | | | | | |
| Control assay without org. compound | 0.20 | 0 | $10^{4.6}$ | $10^{4.2}$ | $10^{3.7}$ | $10^{1.4}$ | 1 | 0.97 | 0.96 | 0.87 |

| | Water content | Ethanol (g/l) | Bacteriophage X 174-virus titer (PFU) after heating for | | | | |
|---|---|---|---|---|---|---|---|
| | | | 0 | 1 | 3 | 10 | hours |
| Combination acc. to invention of org. compound + water | 0.20 | 0.25 | $10^{5.9}$ | $10^{3.3}$ | $10^{1.8}$ | 0 | |
| Control assay without org. compound | 0.20 | 0 | $10^{5.8}$ | $10^{4.1}$ | $10^{2.8}$ | $10^{1.5}$ | |

From the results presented in Table II, it becomes apparent in detail that, with the control assay according to the mode of operation of U.S. Pat. No. 4,640,834 by using Vaccinia virus as the model virus at a water content of 0.20 of the sample to be investigated, the virus titer was $10^{1.4}$ after ten hours of heating. In contrast, this value had been reached already after three hours when operating according to the invention, i.e., when maintaining an ethanolic atmosphere during inactivation. When using an ethanolic atmosphere according to the invention, the Vaccinia virus was no longer detectable after heating for 10 hours, whereas the virus titer still amounted to $10^{1.4}$ after ten hours of heating without ethanolic atmosphere.

Likewisely superior results over the control assay without ethanol were found when using bacteriophages X 174 as model viruses, i.e., the virus titer of $10^{1.5}$ determined after a 10-hour inactivation period during inactivation without alcohol, had been reached already after 3 hours when operating according to the invention by using alcohol. After ten hours of heating, no virus was detectable according to the method of the invention.

The determination of the Factor VIII activity before and after the heat treatment was effected by the 2-stage test. The residual activity of Factor VIII after heating calculated therefrom was sufficient in all cases.

EXAMPLE 2

A preparation containing coagulation factors II, IX and X was obtained from human plasma by adsorption on DEAE Sephadex, washing of the ion exchanger and elution of the partial prothrombin complex according to the method described in Vox Sang. 33, 37–50 (1977).

The eluate was dialyzed, freeze-dried and from it an aqueous solution of the partial prothrombin complex with a content of 40 mg protein/ml was prepared. 2 ml of this solution were each mixed with a suspension of Vaccinia virus in cell culture medium and with isotonic saline, respectively, were filled in vials and freeze-dried. All the samples were adjusted to a water content of 0.15, and half of the samples were mixed with 0.25 g ethanol per liter of container volume. The closed containers with the freeze-dried partial prothrombin complex—with and without virus—were heated at a temperature of 70° C. for different periods of time. Three samples were each taken before heating as well as after one hour and after three hours of heating, to measure the virus titer on the one hand, and the Factor IX residual activity and water content on the other hand. The determination of the virus titer was effected as described in Example 1.

The determination of the Factor IX activity was effected by adding the sample to be tested to a Factor IX deficiency plasma and determining the activated partial thromboplastin time (1-stage test). The determination of the water content was performed as in Example 1.

The virus titers determined after the heat treatment of the moist lyophilisate with alcohol vapor can be taken from Table III, from which it is apparent that the detection limit of the virus had been reached already after three hours, the Factor IX residual activity having been conserved to a sufficient extent. By comparison, it is apparent that the virus titer decreased only slightly after heating of the moist partial prothrombin complex samples without addition of alcohol.

TABLE III

Kinetics of virus inactivation during heating of a partial prothrombin complex

| | Water content | Temperature °C. | Ethanol content g/l | Vaccinia virus titer ($TCID_{50}$) after heating for | | |
|---|---|---|---|---|---|---|
| | | | | 0 | 1 | 3 h |
| Combination acc. to inv. of org. compound + water | 0.15 | 70 | 0.25 | $10^{6.5}$ | $10^{1.1}$ | $<10^{1}$ |
| Control assay without org. compound | 0.15 | 70 | 0 | $10^{5.9}$ | $10^{5.2}$ | $10^{4.1}$ |

EXAMPLE 3

Two formulations of an aqueous solution of a Factor VIII-containing preparation according to U.S. Pat. No. 4,522,751 were prepared, mixed with calcium ions in the form of calcium chloride and with a Vaccinia virus suspension, and freeze-dried. Once the amount of calcium chloride was 18 mg, once it was 27.5 mg, per g of dry lyophilisate. The freeze-dried Factor VIII concentrates were adjusted to a water content of 0.20, were "gassed" with nitrogen as previously described and were heated at 60° C. in the closed vials for 10 hours. The virus titer was determined after 1, 3 and 10 hours as described in Example 1. The Factor VIII activity was determined at equally treated, yet virus-free samples. In the same manner, the kinetics of the virus titer and of the Factor VIII activity were investigated by applying the method according to the invention, wherein, after adjustment of the water content to 0.20, an ethanol atmosphere of 0.4 g per liter of container volume was maintained in the vial.

As can be taken from the results summarized in Table IV, the combination of the action of alcohol vapor on the moistened lyophilisate leads to a virus inactivation effectiveness considerably improved as compared to the prior art. At the same time, the presence of calcium ions causes the stabilization of the Factor VIII activity with respect to the action of ethanol and water.

solution were mixed with a suspension of Vaccinia virus in cell culture medium and with isotonic saline, respectively, were filled into vials and freeze-dried. The samples were adjusted to the water contents indicated in Table V and were mixed with the amounts indicated in Table V, of different organic compounds. The closed vials were heated at a temperature of 60° C. for different periods of time.

The results with regard to virus inactivation as well as to Factor VIII residual activity are to be taken from Table V. From this it is clearly apparent that, with the control samples (treatment with the respective organic compound at a water content of the powder of below 0.05 or below 5% by weight), the Vaccinia virus titer was reduced by less than one log step after 30 hours of treatment (residual titer about $10^{3.5}$), whereas, with the samples according to the method of the invention (water content of the powder above 0.05 or above 5% by weight) the respective organic compound caused the

TABLE IV

Kinetics of virus inactivation and Factor VIII activity during heating at 60° C. of a freeze-dried Factor VIII preparation in the presence of calcium ions

| | Water content | Ethanol (g/l) | Calcium chloride mg/g powder | Vaccinia virus titer (TCID$_{50}$) after heating for | | | | | Residual Factor VIII activity after heating for | | | |
|---|---|---|---|---|---|---|---|---|---|---|---|---|
| | | | | 0 | 1 | 3 | 10 | 30 h | 0 | 1 | 3 | 10 h |
| Combination acc. to inven. org. compound + water + Ca | 0.20 | 0.4 | 27.5 | $10^{5.0}$ | $10^{4.9}$ | $10^{3.1}$ | $<10^1$ | —* | 1 | 0.9 | 0.9 | 0.8 |
| Control assay without organic compound | 0.20 | 0 | 18 | $10^{5.5}$ | $10^{5.5}$ | $10^{5.3}$ | $10^{4.0}$ | —* | 1 | —* | 0.9 | 0.8 |
| Control assay without water$^x$ and without Ca | 0.02 | 0.63 | 0 | $10^{3.8}$ | —* | —* | $10^{3.3}$ | $10^{2.9}$ | 1 | —* | —* | 0.85 |
| Control assay without org. compound and without Ca | 0.20 | 0 | 0 | $10^{5.5}$ | $10^{5.3}$ | $10^{5.1}$ | $10^{4.4}$ | —* | 0.9 | —* | 0.8 | 0.7 |

*not measured
$^x$"without water" means a water content of below 0.05 (5% by weight)

EXAMPLE 4

An aqueous solution of the Factor VIII preparation described in Example 1 was prepared. 2 ml each of this Vaccinia virus titer to be no longer detectable after 1 to 10 hours of heating (virus titer smaller than $10^1$). After heating, the Factor VIII residual activity was sufficient in all cases.

TABLE V

Influence of various organic compounds on the kinetics of virus inactivation and Factor VIII activity during heating at 60° C. of a freeze-dried Factor VIII preparation

| | Acetic acid ethylester (g/l) | Water content | Vaccinia virus titer (TCID$_{50}$) after heating for | | | | | Residual Factor VIII activity after heating for | | | |
|---|---|---|---|---|---|---|---|---|---|---|---|
| | | | 0 | 1 | 3 | 10 | 30 | 0 | 1 | 3 | 10 h |
| Combination acc. to inv. org. compound + water | 4.8 | 0.10 | $10^{3.0}$ | —* | $10^{2.7}$ | $<10^1$ | —* | 0.90 | 0.80 | 0.66 | 0.53 |
| Combination acc. to inv. org. compound + water | 0.36 | 0.25 | $10^{3.1}$ | $<10^1$ | $<10^1$ | $<10^1$ | —* | 1.02 | 0.93 | 0.68 | 0.60 |
| Control assay without water$^x$ | 0.72 | 0.02 | $10^{4.3}$ | —* | —* | $10^{3.9}$ | $10^{3.4}$ | 1 | —* | —* | 0.90 |

| | Diethyl ether (g/l) | Water content | Vaccinia virus titer (TCID$_{50}$) after heating for | | | | | Residual Factor VIII activity after heating for | | | |
|---|---|---|---|---|---|---|---|---|---|---|---|
| | | | 0 | 1 | 3 | 10 | 30 | 0 | 1 | 3 | 10 h |
| Combination acc. to inv. | 0.43 | 0.25 | $10^{3.2}$ | $10^{2.6}$ | $10^{1.6}$ | $<10^1$ | — | 0.98 | 0.89 | 0.74 | 0.47 |

TABLE V-continued

Influence of various organic compounds on the kinetics of virus inactivation and Factor VIII activity during heating at 60° C. of a freeze-dried Factor VIII preparation

| org. compound + water | | | | | | | | | | | |
|---|---|---|---|---|---|---|---|---|---|---|---|
| Control assay without water[x] | 0.57 | 0.02 | $10^{4.3}$ | — | — | $10^{3.6}$ | $10^{3.5}$ | 1 | — | — | 1.00 |

| | Dimethyl-formamide (g/l) | Water content | Vaccinia virus titer (TCID$_{50}$) after heating for | | | | | Residual Factor VIII activity after heating for | | | |
|---|---|---|---|---|---|---|---|---|---|---|---|
| | | | 0 | 1 | 3 | 10 | 30 | 0 | 1 | 3 | 10 h |
| Combination acc. to inv. org. compound + water | 0.4 | 0.08 | $10^{3.1}$ | — | $10^{2.9}$ | $<10^1$ | — | 1.00 | — | 0.69 | 0.55 |
| Control assay without water[x] | 0.8 | 0.02 | $10^{4.4}$ | — | — | $10^{3.8}$ | $10^{3.1}$ | 1 | — | — | 0.88 |

| | Toluene (g/l) | Water content | Vaccinia virus titer (TCID$_{50}$) after heating for | | | | | Residual Factor VIII activity after heating for | | | |
|---|---|---|---|---|---|---|---|---|---|---|---|
| | | | 0 | 1 | 3 | 10 | 30 | 0 | 1 | 3 | 10 h |
| Combination acc. to inv. org. compound + water | 0.35 | 0.21 | $10^{3.2}$ | $10^{2.9}$ | $10^{1.9}$ | $<10^1$ | — | 1.00 | 0.91 | 0.77 | 0.55 |
| Control assay without water[x] | 0.7 | 0.02 | $10^{4.4}$ | — | — | $10^{3.5}$ | $10^{3.5}$ | 1 | — | — | 0.94 |

| | Chloroform (g/l) | Water content | Vaccinia virus titer (TCID$_{50}$) after heating for | | | | | Residual Factor VIII activity after heating for | | | |
|---|---|---|---|---|---|---|---|---|---|---|---|
| | | | 0 | 1 | 3 | 10 | 30 | 0 | 1 | 3 | 10 h |
| Combination acc. to inv. org. compound + water | 0.9 | 0.25 | $10^{2.9}$ | $10^{1.9}$ | $<10^1$ | $<10^1$ | — | 0.90 | 0.89 | 0.78 | 0.59 |
| Control assay without water[x] | 1.2 | 0.02 | $10^{4.0}$ | — | — | $10^{3.6}$ | $10^{3.4}$ | 1 | — | — | 0.85 |

| | n-Heptane (g/l) | Water content | Vaccinia virus titer (TCID$_{50}$) after heating for | | | | | Residual Factor VIII activity after heating for | | | |
|---|---|---|---|---|---|---|---|---|---|---|---|
| | | | 0 | 1 | 3 | 10 | 30 | 0 | 1 | 3 | 10 h |
| Combination acc. to inv. org. compound + water | 0.4 | 0.25 | $10^{3.4}$ | $10^{1.6}$ | $<10^1$ | $<10^1$ | — | 1.11 | 1.08 | 1.00 | 0.78 |
| Control assay without water[x] | 0.55 | 0.02 | $10^{4.0}$ | — | — | $10^{3.5}$ | $10^{3.8}$ | 1 | — | — | 0.95 |

| | 1,2-Diacetoxy ethane (g/l) | Water content | Vaccinia virus titer (TCID$_{50}$) after heating for | | | | | Residual Factor VIII activity after heating for | | | |
|---|---|---|---|---|---|---|---|---|---|---|---|
| | | | 0 | 1 | 3 | 10 | 30 | 0 | 1 | 3 | 10 h |
| Combination acc. to inv. org. compound + water | 0.45 | 0.25 | $10^{3.0}$ | $<10^1$ | $<10^1$ | $<10^1$ | — | 1.07 | 1.03 | 0.74 | 0.56 |
| Control assay without water[x] | 0.9 | 0.025 | $10^{4.0}$ | — | — | $10^{3.8}$ | $10^{3.0}$ | 1 | — | — | 0.89 |

| | Acetone (g/l) | Water content | Vaccinia virus titer (TCID$_{50}$) after heating for | | | | | Residual Factor VIII activity after heating for | | | |
|---|---|---|---|---|---|---|---|---|---|---|---|
| | | | 0 | 1 | 3 | 10 | 30 | 0 | 1 | 3 | 10 h |
| Combination acc. to inv. org. compound + water | 0.5 | 0.15** | $10^{3.5}$ | $10^{3.2}$ | $10^{1.6}$ | $<10^1$ | — | 0.94 | 0.85 | 0.78 | 0.74 |
| Control assay without water[x] | 0.64 | 0.025** | $10^{3.9}$ | — | — | $10^{3.5}$ | $10^{3.6}$ | 1 | — | — | 0.92 |

*not determined
[x]"without water" = water content of below 0.05 (5% by weight)
**set value, water determination according to Karl Fischer not feasible

What we claim is:
1. A method of inactivating reproducible filterable pathogens in blood plasma products, wherein said blood plasma products are heat treated in solid state, which method comprises the combination of the following consecutive steps:

moistening the blood plasma products with water vapor under vacuum to adjust the blood plasma products to a water content of from 0.08 to 0.40 (8 to 40% by weight), subsequently treating the thus obtained moistened blood plasma products, under vacuum, with an organic compound selected from the group consisting of ethanol, acetic acid ethyl ester, diethyl ether, dimethylformamide, toluene, chloroform, n-heptane, 1,2-diacetoxy ethane and acetone in a closed container, to attain a concentration of from 0.01 to 10 g of the organic compound per liter of container volume, and heat treating the blood plasma products in the closed container at a temperature and for a period of time sufficient to inactivate the reproducible filterable pathogens, the water remaining substantially physically bound to the blood plasma products, while the organic compounds stay in gaseous phase.

2. A method as set forth in claim 1, wherein said heat treatment is carried out in the presence of calcium ions.

3. A method as set forth in claim 1, wherein said heat treatment is carried out at a temperature of from 50° to 80° C.

4. A method of inactivating reproducible filterable pathogens in blood plasma products, wherein said blood plasma products are heat treated in solid state, which method comprises the combination of the following consecutive steps:

moistening the blood plasma products with water vapor under vacuum in a moistening container, to adjust the blood plasma products to a water content of from 0.08 to 0.40 (8 to 40% by weight), equilibrating the thus moistened blood plasma products, placing the equilibrated, moistened blood plasma products into an inactivation container, subsequently introducing, under vacuum, into said inactivation container, an organic compound selected from the group consisting of ethanol, acetic acid ethyl ester, diethyl ether, dimethylformamide, toluene, chloroform, n-heptane, 1,2-diacetoxy ethane and acetone, to attain a concentration of from 0.01 to 10 g of the organic compound per liter of inactivation container volume, and heat treating the blood plasma products in the inactivation container at a temperature and for a period of time sufficient to inactivate the reproducible filterable pathogens, the water remaining substantially physically bound to the blood plasma products, while the organic compounds stay in gaseous phase.

5. A method of inactivating reproducible filterable pathogens in blood plasma products, wherein said blood plasma products are heat treated in solid state, which method comprises the combination of the following consecutive steps:

moistening the blood plasma products with water vapor under vacuum in a moistening container, to adjust the blood plasma products to a water content of from 0.08 to 0.40 (8 to 40% by weight), equilibrating the thus moistened blood plasma products, placing the equilibrated, moistened blood plasma products into an inactivation container, sweeping said inactivation container with dry nitrogen, subsequently introducing, under vacuum, into said inactivation container, an organic compound selected from the group consisting of ethanol, acetic acid ethyl ester, diethyl ether, dimethylformamide, toluene, chloroform, n-heptane, 1,2-diacetoxy ethane and acetone, to attain a concentration of from 0.01 to 10 g of the organic compound per liter of inactivation container volume, introducing dry nitrogen into the inactivation container to obtain ambient pressure therein, and heat treating the blood plasma products in the inactivation container at a temperature and for a period of time sufficient to inactivate the reproducible filterable pathogens, the water remaining substantially physically bound to the blood plasma products, while the organic compounds stay in gaseous phase.

* * * * *